(12) United States Patent
Joo et al.

(10) Patent No.: US 10,792,285 B2
(45) Date of Patent: Oct. 6, 2020

(54) STABILIZED PHARMACEUTICAL COMPOSITION CONTAINING PEMETREXED OR PHARMACEUTICALLY ACCEPTABLE SALT THEREOF

(71) Applicant: Chong Kun Dang Pharmaceutical Corp., Seodaemun-gu, Seoul (KR)

(72) Inventors: Min Jae Joo, Yongin-si (KR); Hye Jin Seo, Yongin-si (KR); Shin Jung Park, Yongin-si (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 302 days.

(21) Appl. No.: 16/061,450

(22) PCT Filed: Dec. 13, 2016

(86) PCT No.: PCT/KR2016/014594
§ 371 (c)(1),
(2) Date: Jun. 12, 2018

(87) PCT Pub. No.: WO2017/105059
PCT Pub. Date: Jun. 22, 2017

(65) Prior Publication Data
US 2020/0261458 A1     Aug. 20, 2020

(30) Foreign Application Priority Data
Dec. 14, 2015  (KR) .................. 10-2015-0178339

(51) Int. Cl.
| | | |
|---|---|---|
| A61K 31/519 | (2006.01) | |
| A61K 47/20 | (2006.01) | |
| A61K 9/08 | (2006.01) | |
| A61P 35/00 | (2006.01) | |

(52) U.S. Cl.
CPC .............. *A61K 31/519* (2013.01); *A61K 9/08* (2013.01); *A61K 47/20* (2013.01); *A61P 35/00* (2018.01)

(58) Field of Classification Search
CPC ........ A61K 31/519; A61K 9/08; A61K 47/20; A61P 35/00

USPC ....................................................... 514/265.1
See application file for complete search history.

(56) References Cited

U.S. PATENT DOCUMENTS

| | | | |
|---|---|---|---|
| 5,344,932 A | 9/1994 | Taylor | |
| 6,686,365 B2 | 2/2004 | Riebesehl et al. | |
| 10,391,052 B2 * | 8/2019 | Hashimoto | ............. A61P 35/00 |
| 2016/0120867 A1 | 5/2016 | Shin et al. | |
| 2017/0007538 A1 * | 1/2017 | Hashimoto | .......... A61K 47/183 |

FOREIGN PATENT DOCUMENTS

| | | |
|---|---|---|
| JP | 2014237607 A | 12/2014 |
| KR | 20150095282 A | 8/2015 |
| WO | 01/56575 A1 | 8/2001 |
| WO | 2013165130 A1 | 11/2013 |
| WO | 2013178214 A1 | 12/2013 |
| WO | 2014084651 A1 | 6/2014 |

OTHER PUBLICATIONS

ALIMTA Prescribing Information, Eli Lilly and Company, 2004, 23 pages.
Chattopadhyay, Shrikanta , et al., "Pemetrexed: Biochemical and Cellular Pharmacology, Mechanisms, and Clinical Applications", Mol Cancer Ther 2007; 6 (2), Feb. 2007, 15 pages.

* cited by examiner

*Primary Examiner* — Venkataraman Balasubramanian
(74) *Attorney, Agent, or Firm* — Serville Whitney LLC

(57) ABSTRACT

The present invention relates to a pharmaceutical composition with enhanced stability, containing pemetrexed or a salt thereof, and a preparation method therefor. The present invention provides an injection preparation in liquid form containing pemetrexed, capable of ensuring sufficient stability during circulation and storage by selection of an optimum material and setting of an optimum concentration range in order to secure the stability of pemetrexed. The present invention can provide a pemetrexed preparation which is readily commercially prepared, can prevent microbial contamination occurring during lyophilization or reconstitution, and has enhanced convenience of administration and stability.

25 Claims, No Drawings

STABILIZED PHARMACEUTICAL COMPOSITION CONTAINING PEMETREXED OR PHARMACEUTICALLY ACCEPTABLE SALT THEREOF

CROSS-REFERENCE TO RELATED APPLICATIONS

This application is the National Stage entry of PCT/KR2016/014594, filed on Dec. 13, 2016, which claims priority to Korean Application Number 10-2015-0178339, filed on Dec. 14, 2015, which are incorporated herein by reference in their entireties.

TECHNICAL FIELD

The present invention relates to a stabilized pharmaceutical composition containing pemetrexed or a pharmaceutically acceptable salt thereof, and to a method for producing the same.

BACKGROUND ART

Pemetrexed or a salt thereof (for example, disodium salt) exhibits an anti-cancer effect by inhibiting the activities of metabolites that are involved in a metabolic pathway of folate in various kinds of cancers including mesothelioma and non-small cell lung cancer. As a multitargeted antifolate, pemetrexed is known to target thymidylate synthase (TS) and dihydrofolate reductase (DHFR) when it is activated into polyglutamate derivatives by folylpolyglutamate synthetase (FPGS), after it is introduced to the cells via reduced folate carrier (RFC), which is a major intracellular transport channel for folates (Chattopadhyay, S. et al. 2007. Pemetrexed: Biochemical and cellular pharmacology, mechanisms, and clinical applications. Mol. Cancer Ther. 6, 404-417).

Chemical name of pemetrexed is N-[4-[2-(2-amino-4,7-dihydro-4-oxo-1H-pyrrolo[2,3-d]pyrimidin-5-yl)ethyl]benzoyl]-L-gluatamic acid with the following chemical structure (see, U.S. Pat. No. 5,344,932).

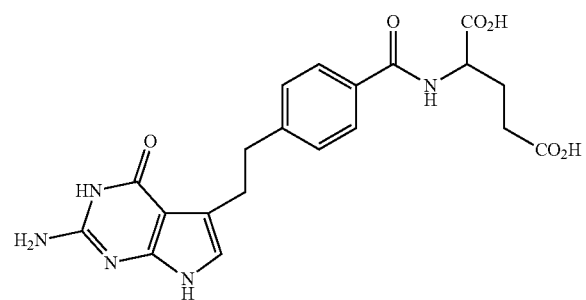 [SMILES: Nc1nc2[nH]cc(CCc3ccc(C(=O)NC(CCC(=O)O)C(=O)O)cc3)c2c(=O)[nH]1]

Presently, pemetrexed is developed under the trade name of ALIMTA®, and in South Korea, it has been marketed since 2007 and used in combination with cisplatin for a patient having inoperable malignant pleuralmesothelioma, who has never received chemotherapy, or it is used as a monotherapy agent for locally advanced breast cancer and non-small cell lung cancer after previously carrying out chemotherapy. ALIMTA® is sold in the market in the form of a lyophilized formulation which needs to be reconstituted prior to administration, i.e., as a formulation in lyophilized powder form (100 mg or 500 mg) that is required to be reconstituted with 0.9% sodium chloride solution and diluted (final concentration at 0.25 mg/ml) finally with 0.9% sodium chloride solution for administration to a patient.

Due to the instability of a pharmaceutical in an aqueous solution phase, an injection preparation of the lyophilized formulation is firstly prepared in lyophilized powder form and used after reconstituting it with physiological saline or water for injection prior to administration to a patient. However, a process for the reconstitution is cumbersome in that the necessary amount needs to be weighed and added to a vial for a lyophilized product, and there is a risk of having microbial contamination during the reconstitution process. Furthermore, there is also a limitation that it needs to be used within a pre-determined time after the reconstitution. Furthermore, because many hours are required due to a long drying cycle of the lyophilization process, the lyophilized formulation has a problem in that it has high production cost and complicated production process. Accordingly, when the economic feasibility of production, user convenience, and the like are considered, there has been a need for a ready-to-use liquid composition having ensured stability.

In many cases, the problem of a liquid preparation lies in the instability during storage period. Due to the instability, many injection preparations are used in lyophilized preparation form which is used after dissolution just before injection. Meanwhile, pemetrexed is a representative example of pharmaceuticals which undergo rapid oxidation in an aqueous solution to yield various kinds of impurities.

As a method of using an anti-oxidant to enhance the stability of a liquid preparation, a liquid pemetrexed preparation containing an anti-oxidant selected from the group consisting of monothioglycerol, L-cysteine, and thioglycoilc acid is known in U.S. Pat. No. 6,686,365 (Korean Patent Application Publication No. 2002-0081293) as a stable pemetrexed solution preparation which contains a therapeutically effective amount of pemetrexed, an effective amount of an anti-oxidant, and a pharmaceutically acceptable excipient. In the examples of the aforementioned patent, a composition using, as an anti-oxidant, 2.4 mg/mL monothioglycerol, 0.03% L-cysteine, and thioglycoilc acid is described. However, a stability improvement level based on a specific experimental example like safety evaluation is not given therein. Furthermore, optimum type and optimum concentration of the anti-oxidant are not selected by specific examples. Still furthermore, when the inventors of the present invention evaluated the safety by reproducing the examples of the aforementioned patent, results like a change in properties like discoloration, an increase in impurities, or the like are exhibited within 4 weeks of storage after carrying out a safety test under accelerated conditions (40° C., 75% RH) in all the examples. As such, the inventors of the present invention acknowledged a need for developing a more specific and advanced technique for allowing supply of a liquid formulation containing pemetrexed, which has sufficient stability during circulation and storage, and thus they started the study on the present invention.

Furthermore, in Korean Patent Registration No. 1260636, a preparation having enhanced stability by using acetyl cysteine as an anti-oxidant and citric acid as a buffer agent with pemetrexed is disclosed, and in Korean Patent Application Publication No. 2013-0122065, an attempt is made to provide a composition having enhanced stability by containing at least one stabilizing agent selected from sodium sulfide and sodium sulfite as an anti-oxidant. As a result of evaluating the stability of a liquid type which has been prepared according to the examples of the above patent, sufficient stability was not exhibited due to a change in properties like discoloration, an increase in impurities, or the like within 4 weeks at 60° C., and thus it was not recognized as an easily reproducible technique. Furthermore, in the specification, the result of observing the safety only for 4 weeks at 60° C. is described, and there is absolutely no mention of the stability for a period over 4 weeks. Accordingly, the inventors of the present invention intended to provide a technique that is easily reproducible and enables the stability for 3 months or longer, and more preferably for a sufficient time period like 6 months at 60° C. or higher.

According to the process of searching various anti-oxidants, the inventors of the present invention found that, among the anti-oxidants that can be used in the pertinent field, monothioglycerol can remarkably enhance the stability of pemetrexed. It is generally known that, when an anti-oxidant is used to suppress the decomposition of a pharmacologically active substance caused by oxidation and an increase in impurities, the safety is enhanced in proportion to the addition amount of an anti-oxidant if it is contained at certain level or higher. However, unlike the descriptions given in prior patent inventions, the inventors of the present invention found that there is a negative effect of monothioglycerol on the stability of pemetrexed when monothioglycerol is present at concentration of 1.50 mg/mL or higher. As such, by selecting an optimum material and also setting an optimum concentration for ensuring the stability of pemetrexed, the inventors of the present invention succeeded in providing a liquid injection preparation containing pemetrexed which allows securing of sufficient stability during circulation and storage and also is stable for 3 months or longer, and more preferably 6 months or longer at 60° C. Consequently, it becomes possible to supply a liquid pemetrexed preparation of which stability can be maintained for a long period of time at high temperatures.

It is also required to minimize a contact with oxygen to secure the stability of a pharmaceutical which is decomposed according to an oxidation mechanism. As such, to reduce the decomposition of pemetrexed resulting from a contact with oxygen, the amount of dissolved oxygen present in solution and oxygen content in the headspace of a vial need to be controlled. As a result of various trials, the inventors of the present invention confirmed that sufficient stability can be obtained when the oxygen content of a liquid composition provided by the present invention is controlled to about 1.5% or less, and preferably 1.0% or less in the headspace of a vial. In this regard, a method of filling inert gas (for example, nitrogen and argon) as a separator in the headspace of a vial is employed.

As a result, according to selection of an optimum anti-oxidant and setting of an optimum concentration of an anti-oxidant and standard oxygen concentration in the headspace of a vial, it becomes possible to provide a liquid formulation containing pemetrexed which has remarkable stability when compared to a known technique and can be stably provided as a commercially available product.

SUMMARY OF THE INVENTION

Problems to be Solved by the Invention

In consideration of the problems that are described above or the like, the inventors of the present invention conducted various studies for improving the stability of a pharmaceutical composition containing pemetrexed or a salt thereof in the form of a solution for injection, and according to the processes of screening various anti-oxidants, the inventors found that monothioglycerol has an excellent anti-oxidant effect while it uniquely shows a decreased anti-oxidant effect at the concentration of 1.50 mg/mL or higher. By also setting the standard for dissolved oxygen in the composition constituting the present invention and oxygen content in the headspace of a vial, the stability is further enhanced.

Means for Solving Problem

To secure the safety of pemetrexed in a solution state, the present invention provides a liquid preparation for injection containing pemetrexed, which is prepared by dissolving pemetrexed or a pharmaceutically acceptable salt thereof in an aqueous solvent, having monothioglycerol at concentration of 0.50 to 1.25 mg/mL as an anti-oxidant, and, after filling with a pharmaceutical solution, controlling oxygen in the headspace of the vial to 1.5% or less, and preferably 1.0% or less.

According to the present invention, the concentration of pemetrexed or a pharmaceutically acceptable salt thereof is about 1 to 100 mg/mL, preferably 20 to 100 mg/mL, and most preferably 25 mg/mL.

According to U.S. Pat. No. 6,686,365 (Korean Patent Application Publication No. 2002-0081293), use of monothioglycerol as an anti-oxidant is suggested as a way of ensuring the stability of pemetrexed in the form of a solution and a liquid preparation containing 2.4 mg/mL of monothioglycerol is simply disclosed in the examples. Namely, specific experimental results relating to the stability are not provided. On the contrary, the absence of anti-oxidant effect at the above concentration is confirmed by the process of the present invention. It is also disclosed that the anti-oxidant effect is exhibited when monothioglycerol is contained at certain concentration or higher.

Based on the experiments using various concentration ranges over a long period of time, the inventors of the present invention confirmed that the optimum anti-oxidant effect is shown when monothioglycerol is contained at 1.25 mg/mL or lower, and if monothioglycerol is contained at concentration higher than that, the anti-oxidant effect is significantly reduced. Furthermore, because lower side effect of a liquid preparation on a human body and lower production cost can be obtained by reducing the content of an anti-oxidant, it is found that monothioglycerol needs to be contained at a concentration of at least 0.50 mg/mL in order to maintain the aforementioned advantages while maintaining an excellent anti-oxidant effect. Accordingly, it is found that the stability of pemetrexed is significantly enhanced in a liquid composition which contains monothioglycerol at a concentration of 0.5 mg/mL to 1.25 mg/mL, preferably 0.50 to 1.00 mg/mL, and most preferably 0.50 to 0.80 mg/mL.

Furthermore, the stability of pemetrexed is significantly enhanced in a liquid composition in which pemetrexed or a pharmaceutically acceptable salt thereof as an active ingredient and monothioglycerol as an anti-oxidant are contained at a ratio of about 20:1 to 50:1, and preferably about 25:1 to 50:1.

As a way of minimizing the decomposition of pemetrexed caused by a contact with oxygen, by setting the dissolved oxygen amount in solution at 0.5 ppm or lower and setting the oxygen content in the headspace of the vial at about 1.5% or lower, and preferably about 1.0% or lower, a liquid type injection preparation containing pemetrexed with sufficient stability during circulation and storage can be provided.

According to an evaluation based on product quality management standards, the preparation provided by the present invention is confirmed to have the stability that is equivalent to the stability of an existing injection formulation in solid form, in terms of an increase in decomposition products including discoloration for 3 months or longer, and preferably for 6 months at severe (60° C.) stability conditions.

The pemetrexed preparation of the present invention contains pemetrexed or a pharmaceutically acceptable salt thereof as an active ingredient.

As described herein, the expression "pemetrexed" indicates a 5-substituted pyrrolo[2,3-d]pyrimidine compound specifically represented by the following chemical formula 1, and it means a multitargeted antifolate which exhibits an anti-cancer effect in various kinds of cancers including non-small cell lung cancer and malignant pleuralmesothelioma.

[Chemical formula 1]

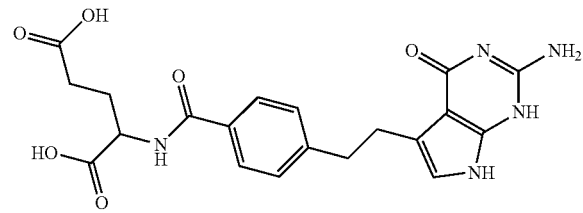

As described herein, the expression "pharmaceutically acceptable salt" means a salt that is produced by a method commonly used in the pertinent art field. Specifically, the pharmaceutically acceptable salt includes salts that are derived from a pharmaceutically acceptable inorganic acid, organic acid, or base, but not limited thereto. In particular, the pharmaceutically acceptable salt of pemetrexed can be a disodium salt of pemetrexed which is currently commercially available, but not limited thereto.

As described herein, the expression "pemetrexed or a pharmaceutically acceptable salt thereof" has a concept of encompassing a hydrate of pemetrexed or a pharmaceutically acceptable salt thereof, and hydrates in any form, for example, 2.5 hydrate, 7 hydrate or the like are included, but not limited thereto.

According to the present invention, the pemetrexed preparation may contain a pharmaceutically acceptable carrier and a pH controlling agent.

According to the present invention, the pemetrexed preparation is preferably a liquid preparation that is storable in a solution state, and it is more preferably a ready-to-use liquid preparation for injection contained in a sealed container.

According to the present invention, when the pemetrexed preparation is a liquid preparation for injection, the pharmaceutically acceptable carrier is water for injection.

For producing the preparation of the present invention, inert gas such as nitrogen or argon can be used to remove, by deaeration, dissolved oxygen in a solution for injection. Methods for the deaeration can be used in combination, and vacuum deaeration and $N_2$ bubbling deaeration, vacuum deaeration and membrane deaeration, or vacuum deaeration and catalyst resin deaeration or the like can be used in combination, for example. Furthermore, the deaeration can be carried out one or more times.

According to the present invention, pH of the liquid pemetrexed preparation for injection is preferably about 6.0 to 8.0, and more preferably about 7.2 to 7.8. pH of the solution can be adjusted by using an acid like hydrochloric acid or a base like sodium hydroxide.

The pemetrexed preparation of the present invention may not contain an additive other than monothioglycerol described above. However, it may additionally contain a pharmaceutically acceptable excipient. As for the pharmaceutically acceptable excipient, a well-known additive such as lactose, dextrose, cyclodextrin and derivatives thereof, sucrose, glycerol, or sodium carbonate can be mentioned. Preferred examples of the excipient include sodium chloride and mannitol, but not limited thereto.

The stabilized pemetrexed-containing solution for injection of the present invention can be packaged in a suitable container that is known in the pertinent art field. Examples of a suitable container include a glass vial, a glass bottle, a cartridge, a pre-filled syringe, and anything similar to them, and it is preferably a glass vial.

The preparation is dispensed by adding it in a container which has been washed and sterilized in advance and sealed with a Teflon stopper of which surface is suitable for the container and inert to the aqueous pemetrexed solution. The stopper is attached by using a crimper.

Effect of the Invention

According to the present invention, a pemetrexed preparation which is readily commercially prepared, can prevent microbial contamination occurring during lyophilization or reconstitution, and has enhanced convenience of administration and stability can be provided. Specifically, based on selection of an optimum anti-oxidant, setting of an optimum concentration of the anti-oxidant, and management of oxygen concentration in the headspace of the vial for maximizing the stability of pemetrexed in a solution, the stability is significantly enhanced compared to a publicly known technique. Finally, by using the present invention, a pemetrexed-containing injection preparation in liquid form, which has sufficient stability during circulation and storage and is stable for 3 months or longer, and preferably for 6 months at 60° C., can be supplied.

BEST MODES FOR CARRYING OUT THE INVENTION

The present invention is more specifically explained in view of Examples. However, the Examples are provided for illustrative purpose only to aid the understanding of the present invention, and it is evident that the scope of the present invention is not limited by the following Examples.

EXAMPLES

Examples 1 to 4 and Comparative Examples 1 and 2: Production of Pemetrexed-Containing Solution for Injection According to Various Anti-Oxidant Concentrations D-Mannitol (25 g) was dissolved in 1,000 mL of water for injection, and monothioglycerol was added at the concentration of the following Table 1 and completely dissolved therein. To the resultant, 30.206 g (25 g in terms of pemetrexed) of pemetrexed disodium 2.5 hydrate were slowly added and stirred till to have transparency. The resulting solution was subjected to sterile filtration by using a sterilized 0.22 μm membrane filter, and dissolved oxygen concentration in the solution after filtration was adjusted to about 0.5 ppm by nitrogen purging. pH of the all solutions prepared according to Examples 1 to 4 and Comparative examples 1 and 2 was measured to be 7.6. The solution obtained from above was filled in a vial, and after controlling the oxygen concentration in the headspace of the vial using nitrogen, it was sealed with a rubber stopper and capped with an aluminum cap to have each of Examples 1 to 4, and Comparative examples 1 and 2.

TABLE 1

|  | Concentration of main component (mg/mL) | Antioxidant | Concentration of antioxidant (mg/mL) | Dissolved oxygen amount (ppm) | Oxygen concentration in headspace of vial (%) |
|---|---|---|---|---|---|
| Example 1 | 25 | monothioglycerol | 0.50 | 0.5 or less | 1.0 or less |
| Example 2 | 25 | monothioglycerol | 0.75 | 0.5 or less | 1.0 or less |
| Example 3 | 25 | monothioglycerol | 1.00 | 0.5 or less | 1.0 or less |
| Example 4 | 25 | monothioglycerol | 1.25 | 0.5 or less | 1.0 or less |
| Comparative example 1 | 25 | monothioglycerol | 1.50 | 0.5 or less | 1.0 or less |
| Comparative example 2 | 25 | monothioglycerol | 0.10 | 0.5 or less | 1.0 or less |

Examples 3, 5 and 6, and Comparative Examples 3 and 4: Production of Pemetrexed-Containing Solution for Injection According to Various Oxygen Concentrations in Headspace of Vial According to various oxygen concentrations in the headspace of the vial as shown in the following Table 2, a pemetrexed-containing solution for injection was produced in the same manner as Example 3 above.

TABLE 2

|  | Concentration main of component (mg/mL) | Antioxidant | Concentration of antioxidant (mg/mL) | Dissolved oxygen amount (ppm) | Oxygen concentration in headspace of vial (%) |
|---|---|---|---|---|---|
| Example 5 | 25 | monothioglycerol | 1.00 | 0.5 or less | 0.5 |
| Example 3 | 25 | monothioglycerol | 1.00 | 0.5 or less | 1.0 |
| Example 6 | 25 | monothioglycerol | 1.00 | 0.5 or less | 1.5 |
| Comparative example 3 | 25 | monothioglycerol | 1.00 | 0.5 or less | 2.0 |
| Comparative example 4 | 25 | monothioglycerol | 1.00 | 0.5 or less | 5.0 |

Comparative Examples 5 to 10: Production of Pemetrexed-Containing Solution for Injection According to Type of Anti-Oxidant According to the composition and content shown in the following Table 3, a pemetrexed-containing solution for injection was produced in the same manner as Example 3 above. In Comparative example 5, the production was made by using a solution in which only deaerated water for injection is used as a solvent without adding an anti-oxidant.

TABLE 3

|  | Concentration of main component (mg/mL) | Antioxidant | Concentration of antioxidant (mg/mL) | Dissolved oxygen amount (ppm) | Oxygen concentration in headspace of vial (%) |
|---|---|---|---|---|---|
| Comparative example 5 | 25 | — | — | 0.5 or less | 1.0 or less |
| Comparative example 6 | 25 | L-Cysteine | 1.00 | 0.5 or less | 1.0 or less |
| Comparative example 7 | 25 | Thioglycolic acid | 1.00 | 0.5 or less | 1.0 or less |
| Comparative example 8 | 25 | EDTA | 1.00 | 0.5 or less | 1.0 or less |
| Comparative example 9 | 25 | Sodium sulfite | 1.00 | 0.5 or less | 1.0 or less |
| Comparative example 10 | 25 | Sodium sulfide | 1.00 | 0.5 or less | 1.0 or less |

[Stability Test]

For the compositions which have been obtained from Examples 1 to 6 according to the present invention, and also from Comparative examples 1 to 10, 6-month stability test was carried out at accelerated conditions (40° C., 75% RH) and severe conditions (60° C.). For the stability test, the amount of impurities which remain in the aqueous solution was analyzed and measured according to the following method in addition to observation of the characteristics of the aqueous solution.

Conditions for HPLC Liquid Chromatography of Impurities
  Detector: UV-Visible spectrophotometer (measurement wavelength: 250 nm)
  Column: Zorbax SB-C8 (4.6 mm×15 cm, 3.5 μm) or equivalent column
  Injection amount: 20 μL
  Flow rate: 1.0 mL/minute
  Column temperature: 35° C.
  Temperature for liquid detection: Constant temperature near 2~8° C.
  Mobile phase A—Mixture liquid of acetate buffer[1]: acetonitrile (97:3)
  Mobile phase B—Mixture liquid of acetate buffer[1]: acetonitrile (87.5:12.5)
  [1] Acetate buffer (0.03 mol/L, pH 5.5): Liquid obtained by adding 3.4 mL of acetic acid per 2 liter of water followed by thorough mixing and adjustment of pH to pH 5.5 by using 50% sodium hydroxide.

TABLE 4

| Time (minutes) | Mobile phase A (%) | Mobile phase B (%) |
|---|---|---|
| 0 | 100 | 0 |
| 40 | 0 | 100 |
| 45 | 0 | 100 |
| 47 | 100 | 0 |
| 55 | 100 | 0 |

Test Example 1. Accelerated Stability Test (6 Month Stability Evaluation at 40° C., 75% RH)

As described in the above, the results of carrying out for 6 months an accelerated stability test (40° C., 75% RH) for the composition obtained from Examples 1 to 6 and Comparative examples 1 to 10 are expressed in Tables 5 to 7. As for the evaluation standard of the stability test, maintaining "colorless" to "light pale yellow" was set as a standard for the characteristics, and total impurities of 1.5% or less and individual impurity of 0.24% or less were set as a standard, which are the same as the management standards for impurity previously known to be generated by oxidation.

TABLE 5

| | Monothioglycerol concentration (mg/mL) | Time | Characteristics | Total impurities (%) | Individual impurity (%) |
|---|---|---|---|---|---|
| Example 1 | 0.50 | Initial state | Colorless | 0.04 | 0.04 |
| | | 4 Weeks | Colorless | 0.25 | 0.10 |
| | | 3 Months | Colorless | 0.38 | 0.14 |
| | | 6 Months | Colorless | 0.46 | 0.15 |
| Example 2 | 0.75 | Initial state | Colorless | 0.08 | 0.07 |
| | | 4 Weeks | Colorless | 0.14 | 0.09 |
| | | 3 Months | Colorless | 0.20 | 0.11 |
| | | 6 Months | Colorless | 0.26 | 0.13 |
| Example 3 | 1.00 | Initial state | Colorless | 0.08 | 0.07 |
| | | 4 Weeks | Colorless | 0.09 | 0.08 |
| | | 3 Months | Colorless | 0.18 | 0.10 |
| | | 6 Months | Colorless | 0.24 | 0.11 |
| Example 4 | 1.25 | Initial state | Colorless | 0.11 | 0.09 |
| | | 4 Weeks | Colorless | 0.12 | 0.10 |
| | | 3 Months | Colorless | 0.18 | 0.12 |
| | | 6 Months | Light pale yellow | 0.36 | 0.23 |
| Comparative example 1 | 1.50 | Initial state | Colorless | 0.09 | 0.08 |
| | | 4 Weeks | Light pale yellow | 0.61 | 0.20 |
| | | 3 Months | Light yellow | 0.95 | 0.36 |
| | | 6 Months | Light yellow | 1.21 | 0.52 |
| Comparative example 2 | 0.10 | Initial state | Colorless | 0.05 | 0.05 |
| | | 4 Weeks | Light pale yellow | 0.56 | 0.13 |
| | | 3 Months | Light yellow | 0.71 | 0.24 |
| | | 6 Months | Light yellow | 0.94 | 0.30 |

As it can be confirmed from the results of Table 5 above, when monothioglycerol is contained at 0.50 to 1.25 mg/mL approximately as an anti-oxidant, the individual impurity (standard: 0.24% or less) and total impurities (standard: 1.5% or less) were maintained at the standard level or lower during 6-month period of the accelerated stability test, exhibiting excellent stability (Examples 1 to 4). On the other hand, when monothioglycerol concentration is within a range of 0.10 mg/mL (Comparative example 2) or less, or 1.50 mg/mL (Comparative example 1) or more, it was found that the individual impurity exceeds the standard with a change in the characteristics (i.e., discoloration).

TABLE 6

| | Oxygen concentration in headspace of vial (%) | Time | Characteristics | Total impurities (%) | Individual impurity (%) |
|---|---|---|---|---|---|
| Example 5 | 0.5 | Initial state | Colorless | 0.08 | 0.07 |
| | | 4 Weeks | Colorless | 0.14 | 0.09 |
| | | 3 Months | Colorless | 0.22 | 0.10 |
| | | 6 Months | Colorless | 0.26 | 0.11 |
| Example 3 | 1.0 | Initial state | Colorless | 0.08 | 0.07 |
| | | 4 Weeks | Colorless | 0.09 | 0.08 |
| | | 3 Months | Colorless | 0.18 | 0.10 |
| | | 6 Months | Colorless | 0.24 | 0.11 |
| Example 6 | 1.5 | Initial state | Colorless | 0.09 | 0.08 |
| | | 4 Weeks | Colorless | 0.14 | 0.09 |
| | | 3 Months | Colorless | 0.20 | 0.11 |
| | | 6 Months | Colorless | 0.26 | 0.12 |
| Comparative example 3 | 2.0 | Initial state | Colorless | 0.09 | 0.08 |
| | | 4 Weeks | Light pale yellow | 0.46 | 0.20 |
| | | 3 Months | Light yellow | 0.81 | 0.63 |

TABLE 6-continued

| | Oxygen concentration in headspace of vial (%) | Time | Characteristics | Total impurities (%) | Individual impurity (%) |
|---|---|---|---|---|---|
| | | 6 Months | Yellow | 1.10 | 0.92 |
| Comparative example 4 | 5.0 | Initial state | Colorless | 0.10 | 0.09 |
| | | 4 Weeks | Yellow | 2.32 | 1.32 |
| | | 3 Months | Yellow | 3.08 | 1.59 |
| | | 6 Months | Yellow | 3.56 | 1.82 |

As it can be confirmed from the results of Table 6 above, when the oxygen concentration in the headspace of the vial is 1.5% v/v or lower, the individual impurity (standard: 0.24% or less) and total impurities (standard: 1.5% or less) were maintained at the standard level or lower during 6-month period of the accelerated stability test, exhibiting excellent stability (Examples 3, 5 and 6). On the other hand, when the oxygen concentration in the headspace of the vial is higher than the aforementioned concentration (Comparative examples 3 and 4), it was found that the impurities exceed greatly the standard with a change in the characteristics (i.e., discoloration).

TABLE 7

| | Antioxidant | Time | Characteristics | Total impurities (%) | Individual impurity (%) |
|---|---|---|---|---|---|
| Comparative example 5 | — | Initial state | Colorless | 0.08 | 0.07 |
| | | 4 Weeks | Yellow | 1.46 | 0.80 |
| | | 3 Months | Deep yellow | — | — |
| Comparative example 6 | L-Cysteine | Initial state | Colorless | 0.09 | 0.08 |
| | | 4 Weeks | Yellow | 0.80 | 0.46 |
| | | 3 Months | Deep yellow | — | — |
| Comparative example 7 | Thioglycolic acid | Initial state | Colorless | 0.10 | 0.08 |
| | | 4 Weeks | Yellow | 1.34 | 0.39 |
| | | 3 Months | Deep yellow | — | — |
| Comparative example 8 | EDTA | Initial state | Colorless | 1.20 | 0.53 |
| | | 4 Weeks | Yellow | 3.02 | 1.38 |
| | | 3 Months | Deep yellow | — | — |
| Comparative example 9 | Sodium sulfite | Initial state | Colorless | 0.09 | 0.08 |
| | | 4 Weeks | Yellow | 1.70 | 0.56 |
| | | 3 Months | Deep yellow | — | — |
| Comparative example 10 | Sodium sulfide | Initial state | Colorless | 0.09 | 0.07 |
| | | 4 Weeks | Yellow | 1.46 | 0.48 |
| | | 3 Months | Deep yellow | — | — |

As it can be confirmed from the results of Table 7 above, when an anti-oxidant is not contained or a conventionally used common anti-oxidant is contained, a change in the characteristics (i.e., discoloration) is shown or the amount of individual impurity and total impurities exceed the standard after 1 month of the accelerated stability test. Furthermore, just 3 months after the storage, discoloration into deep yellow color was shown, and thus no further observation was carried out thereafter. Namely, it was confirmed that the use of monothioglycerol for producing a pemetrexed-containing composition solution for injection yields significantly higher stability compared to a case of using L-cysteine, sodium sulfite, sodium sulfide, or the like.

Test Example 2. Severe Stability Test (6 Month Stability Evaluation at 60° C.)

As described in the above, the results of carrying out for 6 months a severe stability test (60° C.) for the composition obtained from Examples 1 to 6 and Comparative examples 1 to 4 are expressed in Tables 8 and 9. As for the evaluation standard of the stability test, maintaining "colorless" to "light pale yellow" was set as the standard for characteristics, and total impurities of 1.5% or less and individual impurity of 0.24% or less were set as the standard, which are the same as the management standards for impurity previously known to be generated by oxidation.

TABLE 8

| | Monothioglycerol concentration (mg/mL) | Time | Characteristics | Total impurities (%) | Individual impurity (%) |
|---|---|---|---|---|---|
| Example 1 | 0.50 | Initial state | Colorless | 0.04 | 0.04 |
| | | 4 Weeks | Colorless | 0.26 | 0.12 |
| | | 3 Months | Colorless | 0.48 | 0.13 |
| | | 6 Months | Colorless | 0.51 | 0.13 |
| Example 2 | 0.75 | Initial state | Colorless | 0.08 | 0.07 |
| | | 4 Weeks | Colorless | 0.24 | 0.09 |
| | | 3 Months | Colorless | 0.42 | 0.15 |
| | | 6 Months | Colorless | 0.81 | 0.20 |
| Example 3 | 1.00 | Initial state | Colorless | 0.08 | 0.07 |
| | | 4 Weeks | Colorless | 0.34 | 0.13 |
| | | 3 Months | Colorless | 0.65 | 0.17 |
| | | 6 Months | Colorless | 0.72 | 0.19 |
| Example 4 | 1.25 | Initial state | Colorless | 0.11 | 0.09 |
| | | 4 Weeks | Colorless | 0.10 | 0.09 |
| | | 3 Months | Colorless | 0.15 | 0.12 |
| | | 6 Months | Light pale yellow | 1.08 | 0.23 |
| Comparative example 1 | 1.50 | Initial state | Colorless | 0.09 | 0.08 |
| | | 4 Weeks | Yellow | 1.49 | 0.34 |
| | | 3 Months | Yellow | 2.24 | 1.78 |
| | | 6 Months | Deep yellow | — | — |
| Comparative example 2 | 0.10 | Initial state | Colorless | 0.05 | 0.05 |
| | | 4 Weeks | Light yellow | 0.74 | 0.13 |
| | | 3 Months | Yellow | 1.68 | 0.32 |
| | | 6 Months | Yellow | 1.97 | 0.68 |

As it can be confirmed from the results of Table 8 above, when monothioglycerol is contained at 0.50 to 1.25 mg/mL approximately as an anti-oxidant, the individual impurity (standard: 0.24% or less) and total impurities (standard: 1.5% or less) were maintained at the standard level or lower during 6-month period of the severe stability test, exhibiting excellent stability (Examples 1 to 4). On the other hand, when monothioglycerol concentration is within a range of 0.10 mg/mL (Comparative example 2) or less, or 1.50 mg/mL (Comparative example 1) or more, discoloration into deep yellow color was shown 6 months after the storage, and thus the measurement of the amount of impurities was no longer carried out.

TABLE 9

| | Oxygen concentration in headspace of vial (%) | Time | Characteristics | Total impurities (%) | Individual impurity (%) |
|---|---|---|---|---|---|
| Example 5 | 0.5 | Initial state | Colorless | 0.08 | 0.07 |
| | | 4 Weeks | Colorless | 0.19 | 0.11 |
| | | 3 Months | Colorless | 0.21 | 0.14 |
| | | 6 Months | Colorless | 0.31 | 0.17 |
| Example 3 | 1.0 | Initial state | Colorless | 0.08 | 0.07 |
| | | 4 Weeks | Colorless | 0.34 | 0.13 |
| | | 3 Months | Colorless | 0.65 | 0.17 |
| | | 6 Months | Colorless | 0.72 | 0.19 |
| Example 6 | 1.5 | Initial state | Colorless | 0.09 | 0.08 |
| | | 4 Weeks | Colorless | 0.19 | 0.11 |
| | | 3 Months | Colorless | 0.33 | 0.16 |
| | | 6 Months | Colorless | 1.08 | 0.18 |
| Comparative example 3 | 2.0 | Initial state | Colorless | 0.09 | 0.08 |
| | | 4 Weeks | Light yellow | 0.79 | 0.25 |
| | | 3 Months | Yellow | 1.25 | 0.84 |
| | | 6 Months | Deep yellow | — | — |
| Comparative example 4 | 5.0 | Initial state | Colorless | 0.10 | 0.09 |
| | | 4 Weeks | Yellow | 3.17 | 1.79 |
| | | 3 Months | Deep yellow | — | — |
| | | 6 Months | Deep yellow | — | — |

As it can be confirmed from the results of Table 9 above, when the oxygen concentration in the headspace of the vial is 1.5% v/v or less, the individual impurity (standard: 0.24% or less) and total impurities (standard: 1.5% or less) were maintained at the standard level or lower during 6-month period of the severe period of 6 months, exhibiting excellent stability (Examples 3, 5, and 6). On the other hand, when the oxygen concentration in the headspace of the vial is higher than the aforementioned concentration (Comparative examples 3 and 4), a change in the characteristics (i.e., discoloration) was shown and the impurities are significantly higher than the 3-month severe storage standard.

In a case in which the oxygen concentration in the headspace of the vial is 2.0% (Comparative example 3) or 5.0% (Comparative example 4), discoloration into deep yellow color was shown 6 months and 3 months after the storage, respectively, and thus no further measurement of the amount of impurities was carried out. It was accordingly recognized that, when monothioglycerol as an anti-oxidant is contained within a specific concentration range and oxygen concentration in the headspace of the vial is kept at 1.5% or less for producing a solution for injection which contains pemetrexed and a salt thereof, a formulation having remarkably improved stability not only at general temperature conditions but also at severe storage condition of 60° C. can be obtained.

The invention claimed is:

1. A composition comprising pemetrexed or a pharmaceutically acceptable salt thereof as an active ingredient and 0.50 mg/mL to 1.25 mg/mL of monothioglycerol as an antioxidant.

2. The composition according to claim 1, wherein monothioglycerol as an antioxidant is comprised at the amount of 0.50 to 1.00 mg/mL.

3. The composition according to claim 2, wherein monothioglycerol as an antioxidant is comprised at the amount of 0.50 to 0.80 mg/mL.

4. A composition comprising pemetrexed or a pharmaceutically acceptable salt thereof as an active ingredient and monothioglycerol as an antioxidant in which the active ingredient and monothioglycerol are comprised at ratio of about 20:1 to 50:1.

5. The composition according to claim 4, wherein the active ingredient and monothioglycerol are comprised at ratio of about 25:1 to 50:1.

6. The composition according to claim 1, wherein the active ingredient is comprised at the amount of 20 to 100 mg/mL.

7. The composition according to claim 1, wherein the active ingredient is pemetrexed disodium 2.5 hydrate.

8. The composition according to claim 1, wherein the active ingredient is pemetrexed disodium 7 hydrate.

9. A liquid preparation comprising the composition of claim 1 in the form of a solution.

10. The liquid preparation according to claim 9, wherein dissolved oxygen amount in the solution is not more than 0.5 ppm.

11. The liquid preparation according to claim 9, wherein pH of the solution is 6.0 to 8.0.

12. The liquid preparation according to claim 9, wherein the liquid preparation is packaged in a sealed container, and concentration of oxygen contained in the headspace gas of the sealed container is not more than 1.5% v/v.

13. The liquid preparation according to claim 12, wherein the concentration of oxygen contained in the headspace gas of the sealed container is not more than 1.0% v/v.

14. The liquid preparation according to claim 9, wherein an individual impurity is maintained at 0.24% or less and total impurities are maintained at 1.50% or less for 3 months or longer at 40° C. and relative humidity of 75%.

15. The liquid preparation according to claim 9, wherein an individual impurity is maintained at 0.24% or less and total impurities are maintained at 1.50% or less for 3 months or longer at 60° C.

16. A liquid preparation produced by comprising steps of:
dissolving pemetrexed or a pharmaceutically acceptable salt thereof and 0.50 to 1.25 mg/mL of monothioglycerol in water for injection; and
controlling oxygen concentration in headspace gas of a sealed container to 1.5% v/v or less.

17. The composition according to claim 4, wherein the active ingredient is pemetrexed disodium 2.5 hydrate.

18. The composition according to claim 4, wherein the active ingredient is pemetrexed disodium 7 hydrate.

19. A liquid preparation comprising the composition of claim 4 in the form of a solution.

20. The liquid preparation according to claim 19, wherein dissolved oxygen amount in the solution is not more than 0.5 ppm.

21. The liquid preparation according to claim 19, wherein pH of the solution is 6.0 to 8.0.

22. The liquid preparation according to claim 19, wherein the liquid preparation is packaged in a sealed container, and concentration of oxygen contained in the headspace gas of the sealed container is not more than 1.5% v/v.

23. The liquid preparation according to claim 22, wherein the concentration of oxygen contained in the headspace gas of the sealed container is not more than 1.0% v/v.

24. The liquid preparation according to claim 19, wherein an individual impurity is maintained at 0.24% or less and total impurities are maintained at 1.50% or less for 3 months or longer at 40° C. and relative humidity of 75%.

25. The liquid preparation according to claim 19, wherein an individual impurity is maintained at 0.24% or less and total impurities are maintained at 1.50% or less for 3 months or longer at 60° C.

* * * * *